United States Patent
Dahricorreia et al.

(10) Patent No.: US 7,101,863 B2
(45) Date of Patent: Sep. 5, 2006

(54) PHARMACEUTICAL COMPOSITIONS WITH WOUND HEALING OR ANTI-COMPLEMENTARY ACTIVITY COMPRISING A DEXTRAN DERIVATIVE

(75) Inventors: Latifa Dahricorreia, Saint Amand les Eaux (FR); Jacqueline Jozefonvicz, Lamorlaye (FR); Marcel Jozefowicz, Lamorlaye (FR); José Correia, Saint Amand les Eaux (FR); Rémi Huynh, Saint Amand les Eaux (FR)

(73) Assignee: Biodex (FR)

( * ) Notice: Subject to any disclaimer, the term of this patent is extended or adjusted under 35 U.S.C. 154(b) by 593 days.

(21) Appl. No.: 10/020,044

(22) Filed: Dec. 13, 2001

(65) Prior Publication Data
US 2002/0183282 A1 Dec. 5, 2002

Related U.S. Application Data (63) Continuation of application No. PCT/FR00/01658, filed on Jun. 15, 2000.

(51) Int. Cl.
A61K 31/721 (2006.01)
C08B 37/02 (2006.01)

(52) U.S. Cl. .............................. 514/59; 514/54; 536/51
(58) Field of Classification Search .................. 514/54, 514/59; 536/51
See application file for complete search history.

(56) References Cited

U.S. PATENT DOCUMENTS

| | | | |
|---|---|---|---|
| 4,740,594 A | 4/1988 | Mauzac et al. | 536/51 |
| 5,693,625 A | 12/1997 | Barritault et al. | 514/59 |
| 5,852,003 A | 12/1998 | Barritault et al. | 514/54 |

FOREIGN PATENT DOCUMENTS

| WO | WO 95/26736 | 10/1995 |
|---|---|---|

OTHER PUBLICATIONS

Josenfonvicz, J. et al "New Investigations on the heparin-like derivatized dextrans: CMDBS, synergistic role of benzylamide and sulfate substituents in anticoagulant activity", Carbohydrate Poplymers, 1997, 32, 89–93.*

Josenfonvicz, J. et al "Synthesis and structure–anticoagulant property relationships of functionalized dextrans: CMDBS", Carbohydrate Polymers, 1995, 28, 145–152.*

O. Maiga–Revel, et al., "New Investigations on Heparin–Like Derivatized Dextrans: CMDBS, Synergistic Role of Benzylamide and Sulfate Substituents in Anticoagulant Activity," *Carbohydrate Polymers*, 32:89–93 (1997).

Didier Letourneur, et al., "Antiproliferative Capacity of Synthetic Dextrans on Smooth Muscle Cell Growth: The Model of Derivatized Dextrans as Heparin–Like Polymers," *J. Biomater. Sci. Polymer Edn.*, 4: 431–444 (1993).

F. Blanquaert, et al., "Les CMDBS, Analogues Fonctionnels Des Héparanes Sulfates, Utilisés Comme Agents de la Cicatrisation Osseuse (Functional Analogues of Heparin Sulfate Used As Bone Healing Agents)" pp. *Annales d'Endocrinologie (Paris)*, 55: 121–123 (1994), summary considered.

Daniel Stockholm, et al., "Studies on Calpain Expression During Differential of Rat Satellite Cells in Primary Cultures in the Presence of Heparin or a Mimic Compound," *Experimental Cell Research*, 252: 392–400 (1999).

A. Meddahi, et al., "New Approaches to Tissue Regeneration and Repair," *Path. Res. Pract.* 190: 923–928 (1994).

Jean Gautron, et al., "Accélération de la régénération d'un Muscle Squelettique de Rat Adulte par des Dérivés de Dextranes" (Injection of a Heparan Sulfate Like Substance in a Crushed Muscle Accelerates It Regeneration), *C. R. Acad. Sci., Paris, Sciences de la vie (Life Sciences), Bologie Cellulaire (Cell Biology)* 671–676, (1995), Abstract considered.

M. Mauzac and J. Jozenfonvicz, "Anticoagulant Activity of Dextran Derivatives, Part 1: Synthesis and Characterization," *Biomaterials*, 5: 301–304 (Sep. 1984).

Frederic Chaubet, et al., "Synthesis and Structure—Anticoagulant Property Relationships of Functionalized Dextrans; CMDBA," *Carbohydrate Polymers*, vol. 28: 145–152 (1995).

Seikagaku Kogyo CO., LTD., Japanese Patent Abstract No. J49025120 for Application No. 1975–08052W [05] Published Jul. 1, 1972, "Antacid–Carboxymethyl Polysaccharide Complexes—Carboxymethyl Polysaccharides are Reacted With Aluminum Magnesium Silicates.".

\* cited by examiner

*Primary Examiner*—James O. Wilson
*Assistant Examiner*—Ganapathy Krishnan
(74) *Attorney, Agent, or Firm*—Welsh & Katz, Ltd.; Thomas W. Tolpin (57) ABSTRACT

The invention concerns pharmaceutical compositions with wound healing or anti-complementary activity, and their uses, said compositions comprising, (1) at least a dextran derivative of general formula $DMC_aB_bSu_c$, a, b, and c respectively representing the degrees of substitution in the groups MC, B and Su, wherein $a \geq 0.6$, $b=0$ or $\geq 0.1$, and $c=0$ or ranges widely between 0.1 and 0.5 for a wound healing composition, and $a \geq 0.3$, $b \geq 0.1$ and $c=0$ or ranges widely between 0.1 and 0.4 for a composition with anti-complementary activity; (2) and at least a pharmaceutically acceptable carrier, said dextran derivative being present in a single unit dose or at a concentration adapted to the desired wound healing or anti-complementary activity.

11 Claims, 3 Drawing Sheets

PHARMACEUTICAL COMPOSITIONS WITH WOUND HEALING OR ANTI-COMPLEMENTARY ACTIVITY COMPRISING A DEXTRAN DERIVATIVE

This application is a continuation of PCT/FR00/01658 filed Jun. 15, 2000.

BACKGROUND OF THE INVENTION

The present invention relates to pharmaceutical compositions which have a healing or anticomplementary action and which comprise at least one dextran derivative.

Different dextrans which are substituted by side chains carrying carboxylate and sulfonate groups have been described. In particular, dextran derivatives comprising, respectively, 83% or 110% of units substituted by carboxymethyl groups, 23% or 2.6% of units substituted by carboxymethylbenzylamide groups, and 13% or 36.5% of units substituted by sulfonate groups (sulfonate groups carried by the carboxymethylbenzylamide units), namely RGTA9 and RGTA11, respectively, have been described for their action, in vivo in rats, on skin repair (A. Meddahi et al., Path. Res. Pract., 1994, 190, 923–928; A Meddahi et al., Diabetes & Metabolism (Paris), 1996, 22, 274–278) and on muscle regeneration (A. Aamiri et al., Neuroscience Letters, 1995, 201, 243–246; J. Gautron et al., C. R. Acad. Sci. Paris, Life sciences, Cell biology, 1995, 318, 671–6; A. Aamiri et al., C. R. Acad. Sci. Paris, Life sciences, Neurosciences, 1995, 318, 1037–43).

As far as skin repair is concerned, A. Meddahi et al. (ibid) propose making good skin wounds using collagen pieces which have been soaked with a solution of RGTA9 or RGTA11; an improvement in the speed and the quality of skin regeneration is observed under these conditions. This improvement could be explained on the basis that the RGTA9 or RGTA11 trap, protect and release the endogenous growth factors which are naturally secreted during skin healing. Protection of the growth factors would make it possible to avoid their being degraded by the natural proteases, thereby preserving their ability to stimulate tissue repair.

In the field of muscle regeneration, A. Aamiri et al. and J. Gautron et al. (ibid) propose injecting rats, whose rapid muscles (EDL: Extensor Digitorium Longus) and/or slow muscles (soleus) have been crushed, with a solution of RGTA11. They observe an improvement in the regeneration of the muscles following this injection: the treated muscles exhibit a larger number of muscle fibers and more rapid reinnervation.

However, because of the method by which they are prepared, the abovementioned RGTA9 and 11 suffer from the drawback of exhibiting an irregular distribution of chemical (carboxymethyl, carboxymethylbenzylamide and sulfonate) groups and polysaccharide chains, leading to a heterogeneous final product whose properties are difficult to control.

The aim of the inventors has therefore been to select dextran derivatives which differ from the already-described compounds RGTA9 and 11 in order to provide for pharmaceutical compositions which have an anticomplementary or healing action, in particular in the fields of skin, muscle, ocular or gastric mucosal healing, which more satisfactorily meet practical requirements, in particular by exhibiting an increased activity, and which are suitable for administration to humans, this being in forms and at doses which are adjusted for optimum efficacy.

BRIEF SUMMARY OF THE INVENTION

Thus, the inventors have developed pharmaceutical compositions which have a healing and anticomplementary action and which are based on specific dextran derivatives.

The present invention relates to a pharmaceutical composition which has a healing action and which comprises:

(1) At least one dextran derivative of general formula $DMC_aB_bSu_c$, in which:

D represents a polysaccharide chain, preferably consisting of linked glucoside units, MC represents methylcarboxyl groups, B represents carboxymethylbenzylamide groups, Su represents sulfate groups (sulfation of the free hydroxyl functions carried by the glucoside units), a, b and c represent the degree of substitution (ds), expressed in relation to the number of free hydroxyl functions in a glucoside unit of the dextran, with MC, B and Su groups, respectively; a being $\geq 0.6$, b being equal to 0 or $\geq 0.1$ and c being equal to 0 or being, broadly, between 0.1 and 0.5, (2) As well as at least one pharmaceutically acceptable excipient, said dextran derivative being present at a unit dose of between 0.1 and 50 mg.

"Excipient" is understood as being any adjuvant or vehicle which is without pharmacological action but which makes it possible to manufacture, preserve or administer the pharmaceutical composition. Any pharmaceutically acceptable excipient, which is selected, for example, from the excipients which are commonly used in pharmacy, can be employed in the pharmaceutical composition according to the invention having a healing action.

The pharmaceutical composition according to the invention thus comprises dextran derivatives which differ significantly from those described in the prior art under the designations RGTA9 and 11, in particular due to the fact that they do not comprise any sulfonate units.

The above-defined dextran derivatives are regarded as being copolymers which consist of imaginary subunits R—OH and R—OX, where X can be a methylcarboxylate (MC), benzylamide (B) or sulfate (Su) group, the polysaccharide chain of the unsubstituted dextran being regarded as consisting of 300 imaginary R—OH subunits instead of 100 glucoside units, having regard to the fact that an unsubstituted glucoside unit comprises three free hydroxyl groups. Thus, a dextran methylcarboxylate (DMC) having a degree of substitution (ds) of 1.2 in methylcarboxylate groups contains 1.20 substituted (R-MC) group [sic] and 1.80 free hydroxyl (R—OH) group [sic] per glucoside unit. It must, of course, be understood that the sum of the a, b, and c degrees of substitution in the above-defined general formula $DMC_aB_bSu_c$ is less than or equal to 3.

The derivatives of the dextran of general formula $DMC_aB_bSu_c$, as defined above, can be obtained by means of a process which comprises the following steps, as described in French patent 2 772 382:

a) Carboxymethylation comprising (i) the activation of an unsubstituted dextran by bringing said dextran into contact with a basic two-phase liquid water-alcohol medium for at least 1 h, while stirring, (ii) addition of monochloroacetic acid to the resulting activated product, at a temperature of between 40 and 90° C., preferably at 60° C., the RMC ratio, equal to the number of moles of monochloroacetic acid/number of moles of OH, being between 0.3 and 2, (iii)

isolation, and, where appropriate, purification, of the resulting dextran methylcarboxylate (DMC);

b) coupling benzylamine to the methylcarboxylate groups (benzylamidification) comprising (i) bringing the DMC obtained in a) into contact, for at least 2 h and in acid aqueous medium, with a primary amine (benzylamine) in the presence of a water-soluble carbodiimide such as 1-cyclohexyl-3-(2-morpholinoethyl)carbodiimide meta-p-toluenesulfonate (CMC) or 1-ethyl-3-(3-dimethylaminopropyl)carbodiimide hydrochloride (EDC) as coupling agent, at a temperature between 0° C. and 30° C., the water-soluble carbodiimide/MC molar ratio being between 0.25 and 2 and the benzylamine/MC molar ratio being between 0.25 and 2, (ii) isolation of the resulting dextran methyl carboxyl benzylamide (DMCB) and, where appropriate, its purification;

this step, which is carried out in homogeneous medium and in the presence of a water-soluble carbodiimide as coupling reagent, makes it possible to control the reaction and therefore prepare the final product, this latter exhibiting homogeneity in the distribution of the chain sizes, illustrated by an elution profile of the symmetrical Gaussian type in high-performance steric exclusion chromatography, and homogeneity in the distribution of the charged chemical groups, illustrated by an elution profile having a single symmetrical peak in low-pressure ion exchange chromatography; then c) sulfation comprising (i) the formation of a trialkylammonium salt of the DMCB obtained in b), (ii) dissolution of the resulting salt in an anhydrous polar solvent, generally a Lewis base (electron donor) such as dimethyl sulfoxide (DMSO) or dimethylformamide (DMF), and (iii) the addition, to said salt in solution, of a sulfur trioxide-based complex such as $SO_3$-pyridine, $SO_3$-triethylamine or $SO_3$-DMS, in solution in the same solvent, at a temperature of less than 70° C., the sulfur trioxide-based complex/free OHs molar ratio being between 0.25 and 12.

The dextran derivatives obtained in accordance with such a process, and which are used in the pharmaceutical composition according to the invention, exhibit homogeneity in the distribution of the chain sizes, illustrated by an elution profile of the symmetrical Gaussian type in high-performance steric exclusion chromatography, and homogeneity in the distribution of the charged chemical groups, illustrated by an elution profile having a single symmetrical peak in low-pressure ion exchange chromatography. These dextran derivatives are such that the distribution of the chemical groups confers a specific biological property on the final product; the consequence of such a distribution is that the chemical composition of each polysaccharide chain is identical to the global chemical composition of the product. For this reason, an optimum chemical composition is available for a maximum specific biological activity; there is, therefore, a direct relationship between the biological property under consideration and the global chemical composition of the product.

Particularly advantageously, the composition according to the invention, which composition comprises at least one dextran derivative as described above, at the abovementioned unit dose, makes it possible to obtain a particularly efficacious healing action.

This property is linked to the interaction between the dextran derivatives and the growth factors which are naturally secreted at an injured site, as has been demonstrated, in particular, by A. Meddahi et al., in Journal of Biomedical Materials Research, 1996, 31, 293–297, by J. Lafont et al in Growth factors, 1998, 16, 23–38 and by F. Blanquaert et al., in Journal of Biomedical Materials Research, 1999, 44, 63–72. F. Blanquaert et al. (ibid) have shown that a high degree of substitution in sulfonate units is important for ensuring that a dextran derivative interacts with growth factors. Surprisingly, the dextran derivatives used in the pharmaceutical composition according to the invention, and which do not comprise any sulfonate groups, are nevertheless able to protect growth factors, such as FGFs (Fibroblast Growth Factors), TGF-α and β (Transforming Growth Factors), IGFs, EGFs (Epidermal Growth factors) and PDGFs (Patent-Derived Growth factors) from proteolytic degradation and in this way promote their beneficial action on healing.

The invention also relates to the use of the above-defined pharmaceutical composition for preparing a medicament having healing action.

In particular, the invention relates to the use of the above-defined pharmaceutical composition for preparing a medicament which has an action on the healing of the gastricmucosa, in which case the dextran derivative is preferably present in the pharmaceutical composition at a unit dose of between 1.5 and 10 mg.

In this use, the pharmaceutical composition, which is advantageously in the form of a gel, a gastric dressing, a syrup or a potable solution, is suitable for administration by the oral route.

Particularly advantageously, the dextran derivative can be enclosed in a vector which allows it to be released over an extended period or enables it to be released specifically at a given site. The enclosure can, for example, be a gastric juice-resistant enclosure. The invention also relates to the use of the above-defined pharmaceutical composition for preparing a medicament having an action on muscle healing, in which case the dextran derivative is preferably present in the pharmaceutical composition at a unit dose of between 0.5 and 50 mg.

Such a pharmaceutical composition is present, for example, in the form of a gel or an ointment (for use by means of local external application), or else in the form of an isotonic solution, that is to say a solution whose osmotic pressure is the same as that of the blood. In this latter case, the pharmaceutical composition is suitable for being administered by the parenteral route, for example in the form of an intramuscular injection.

The invention also relates to the use of the above-defined pharmaceutical composition for preparing a medicament having an action on ocular healing, in which case the dextran derivative is preferably present in the pharmaceutical composition at a unit dose of between 0.1 and 10 mg.

In this use, the pharmaceutical composition is present in the form, for example, of eye drops or of an ophthalmic ointment.

The present invention also relates to a pharmaceutical composition which has an action on skin healing and which is suitable for being administered topically, this pharmaceutical composition comprising:

(1) at least one dextran derivative of general formula $DMC_aB_bSu_c$ as defined above, (2) and also at least one pharmaceutically acceptable excipient, said dextran derivative being present at a concentration of less than 10% (by weight/volume).

The invention also relates to the use of such a pharmaceutical composition for preparing a medicament which has an action on skin healing and which is intended to be administered topically.

In this use, the pharmaceutical composition can take the form of a paste, an ointment, an aqueous liquid, an oily liquid, an aqueous gel, an oily gel, an aerosol, a foam, a microemulsion, a multiple emulsion, liposomes or nanoparticles.

"Paste" is understood as meaning an anhydrous paste, for example a paste based on propylene glycol, glycerol or stearic acid. An ointment can be obtained by using polyethylene glycol, vaseline or liquid paraffin.

Said pharmaceutical composition could also, for example, take the form of a powder, that is to say a lyophilizate which is suitable for being returned to the form of a solution at the time of its use.

The pharmaceutical composition having an action on skin healing according to the invention can be applied topically (external local route) to the skin wound either directly or by way of a medical device such as a compress, classically a cotton or fabric compress, which is saturated with the composition according to the invention at the above-indicated concentration.

The present invention also relates to a pharmaceutical composition which has an anticomplementary action and which comprises:

(1) at least one dextran derivative of general formula, $DMC_aB_bSu_c$ in which:

D represents a polysaccharide chain which preferably consists of linked glucoside units, MC represents methylcarboxylate groups, B represents carboxymethylbenzylamide groups, Su represents sulfate groups (sulfation of the free hydroxyl functions carried by the glucoside units), a, b, and c represent the degree of substitution (ds), expressed in relation to the number of free hydroxyl functions in a glucoside unit of the dextran, with MC, B and Su groups, respectively; a being $\geq 0.3$, b being $\geq 0.1$ and c being equal to 0 or, broadly, between 0.1 and 0.4, (2) and also at least one pharmaceutically acceptable excipient, said dextran derivative being present at a unit dose of between 5 and 30 mg.

"Excipient" is understood as meaning any adjuvant or vehicle which does not have any pharmacological action but which makes it possible to manufacture, preserve or administer the pharmaceutical composition. Any pharmaceutically acceptable excipient, which is selected, for example, from the excipients which are commonly used in pharmacy, can be employed in the pharmaceutical composition according to the invention having an anticomplementary action.

The pharmaceutical composition according to the invention having an anticomplementary action thus comprises dextran derivatives which are significantly different from those described in the prior art under the designations RGTA9 and 11, with a particular difference being that they do not comprise any sulfonate units.

The dextran derivatives of general formula $DMC_aB_bSu_c$ which are present in the pharmaceutical composition according to the invention having an anticomplementary action are identical to those which were previously described in connection with the pharmaceutical compositions according to the present invention having a healing action. They can, in particular, be obtained by the process described in French patent 2 772 382, in which case they exhibit a homogeneity in the distribution of the chain sizes which is illustrated by an elution profile of the symmetrical Gaussian type in high-performance steric exclusion chromatography, and a homogeneity in the distribution of the charged chemical groups which is illustrated by an elution profile having a single symmetrical peak in low-pressure ion exchange chromatography.

Particularly advantageously, the pharmaceutical composition according to the invention, which comprises at least one dextran derivative as described above, at the abovementioned unit dose, makes it possible to obtain a particularly efficacious anticomplementary action and can be used in all types of diseases or treatments which involve activation of the complement system (autoimmune diseases, graft rejections, plasma or blood dialysis, etc.).

The invention also relates to the use of the above-defined pharmaceutical composition having an anticomplementary action for preparing a medicament having an anticomplementary action.

In this use, the pharmaceutical composition advantageously takes the form of an isotonic solution. It is then administered by injection (for example an intravenous or intramuscular injection).

The present invention additionally relates to a dressing, characterized in that it is saturated with the pharmaceutical composition having an action on skin healing, which composition is suitable for topical administration, as described above.

The bounds of the present invention would not be overstepped by, if necessary, adding pharmaceutically acceptable additives, such as preservatives, antioxidants, antibacterial agents, penetration factors, dyes, sweeteners and flavorings, and also one or more other active principles, for example an antibiotic, to the above-described pharmaceutical compositions having a healing action or an anticomplementary action.

The pharmaceutical compositions according to the invention having a healing or anticomplementary action can be used both in human health and in animal health (that is, within the context of a veterinary usage).

The abovementioned unit doses for the pharmaceutical compositions according to the invention having a healing or anticomplementary action are given with respect to an adult individual weighing approximately 70 kg; however, it will, of course, be understood that the skilled person will adjust these doses in accordance with the weight, the age and the pathology or the symptoms of the individual.

Apart from the abovementioned provisions, the invention additionally comprises other provisions which will be evident from the description which follows and which refers to exemplary embodiments of the process to which the present invention relates, as well as to the attached drawings and appended claims.

DETAILED DESCRIPTION OF THE INVENTION

Pharmaceutical compositions with wound healing and/or anti-complementary activity comprising a dextran derivative according to the preferred embodiments of the present invention will now be explained in view of the following examples. It should, of course, nevertheless be understood that these examples are given solely by way of illustrating the subject matter of the invention, of which they in no way constitute a limitation.

EXAMPLE 1

Absence of sulfonate groups in the different dextran derivatives of general formula $DMC_aB_bSu_c$ which are used in the pharmaceutical compositions according to the present invention.

a) Protocol

The following desulfation protocol, which is suitable for desulfating a variety of products without removing any sulfonate groups which may be present, was performed.

The product, in the form of the sodium salt (250 mg, 10 ml), is slowly stirred at room temperature with 3 ml of cation exchange resin (Amberlite® IR120 H+, 16–45 mesh, total exchange capacity: 1.9 meq/ml). After 2 h, the acid solution is filtered, neutralized with pyridine (1 to 2 ml) to a pH of 6–6.5 and evaporated to dryness. The resulting pyridinium salt is taken up 3 times with 10 ml of anhydrous methanol and evaporated to dryness.

The residue is dispersed in 25 ml of a 90:9:1 mixture of dimethyl sulfoxide (DMSO), methanol and pyridine. The solution is stirred in an oil bath, which is heated at 90° C., for 72 h. The reaction is stopped by adding 20 ml of cold double distilled water and the mixture is then neutralized with an aqueous solution of 1M NaOH. The desulfated product is purified by low-pressure steric exclusion chromatography on a Sephadex® G 15 column and then diafiltered through a cell equipped with a membrane having a cut-off threshold of 1000 Da. Between 160 and 210 mg of desulfated product are obtained.

The products which were subjected to this protocol are dextran derivatives having the following compositions, D, MC, B, Su and S respectively representing the glucoside units of the polysaccharide chain, the methylcarboxylate groups, the carboxymethylbenzylamide groups, the sulfate groups and the sulfonate groups:

A: $DMC_aB_bSu_cS_d$: a=0.87, b=0.16, c=0.5 and d=0.10,

B: $DMC_aB_bSu_cS_d$: a=0.87, b=0.16, c=0.6 and d=0.07,

C: $DMC_aB_bSu_cS_d$: a=0.87, b=0.16, c=1.0 and d=0.05,

D: $DMC_aB_bSu_c$: a=0.81, b=0.18 and c=0.40,

E: $DMC_aB_bSu_c$: a=0.81, b=0.18 and c=0.30,

F: $DMC_aSu_c$: a=0.95 and c=0.48,

G: $DMC_aSu_c$: a=0.95 and c=0.93

The compounds A to C, F and G correspond to reference compounds, whereas the compounds D and E correspond to dextran derivatives which are used in the pharmaceutical compositions according to the invention.

b) Results

Table I represents a compilation of the contents of sulfur, measured by elemental analysis and with respect to 100 g of the dextran derivative, for each of the above-described products A to G before and after desulfation.

TABLE I

| Dextran derivative | Before desulfation. Sulfur (g/100 g) | After desulfation. Sulfur (g/100 g) |
|---|---|---|
| A | 1.91 | 0.43 |
| B | 2.00 | 0.25 |
| C | 3.00 | 0.15 |
| D | 1.18 | 0 |
| E | 0.96 | 0 |
| F | 1.66 | 0 |
| G | 2.80 | 0 |

Following desulfation, sulfur is seen to be totally absent from products D to G, which were prepared using an $SO_3$-pyridine complex, whereas products A to C exhibit a sulfur content which is significantly lower but which is not zero. It therefore follows from these results that the absence of sulfur corresponds to the absence of sulfonate groups.

In order to confirm this result, a sodium salt of sulfanylic acid (sodium salt of para-analine sulfonic acid: $H_2N-C_6H_5-SO_3Na$) was coupled to a dextran derivative of general formula $DMC_a$, in which a=0.95, by following the same procedure as that previously described for coupling benzylamine to a dextran derivative carrying carboxymethyl groups. Therefore, apart from carboxymethyl groups, the resulting derivative only contains sulfonate groups. Its content of sulfur is 1.20 g/100 g. After subjecting this derivative to the above-described desulfation protocol, its sulfur content is 1.08 g/100 g. The sulfonate groups are not therefore globally affected by the desulfation process. The absence of sulfur from the dextran derivatives treated by desulfation therefore does indeed signify an absence of sulfonate groups.

It therefore follows from this example that the dextran derivatives of general formula $DMC_aB_bSu_c$ which are used in the pharmaceutical compositions according to the present invention do not possess any sulfonate groups.

EXAMPLE 2

In-vivo action of a dextran derivative of general formula $DMC_aB_bSu_c$ on skin healing.

a) Protocol

The animals employed are New Zealand albino rabbits which are 1 year of age and which weigh from 3.5 to 4.0 kg. Two batches of animals are used, each consisting of 6 males and 6 females. The first batch is treated with a dextran derivative of general formula $DMC_aB_bSu_c$ in which a=0.80, b=0.20 and c=0.20, whereas the second batch serves as control, the animals only being given a physiological solution.

The protocol adopted is as follows:

two epidermal-dermal skin wounds of 6 mm in diameter are made on either side of the vertebral axis, a compress, which is soaked, in accordance with the animal batches, either with a 50 μg/ml solution of the above-mentioned dextran derivative in a PBS buffer, or with a physiological solution, is applied twice daily to the skin wounds, the wounds and the general state of the animals are examined daily, with the progress of the healing being monitored by taking samples from the wounds at D2, D4, D6, D8, D10, D15 and D30 (the healing process is considered in days from the date on which the skin wounds are made), the samples are prepared in the form of sections and are analyzed by studying them histologically.

b) Results

The different histological phenomena which are observed are summarized in tables II to IV below.

Table II summarizes the state of the extracellular matrix in terms of the number of days of healing, in accordance with the following criteria: presence of inflammatory cells and fibroblasts (0: absence of these cells; +, ++ and +++: presence of these cells, with their number increasing as the number of + signs increases) and characteristics of the blood vessels (+: presence of vessels; 0: absence of vessels; high: vessels studied in the upper part of the histological section; low: vessels studied in the lower part of the histological section, corresponding to the part which is closest to the dermis).

Table II: Extracellular Matrix

TABLE II

| | Extracellular matrix | | | | |
|---|---|---|---|---|---|
| | Inflammatory cells | | Fibroblasts | | Vessels (vs) |
| Days of healing | Treated animals | Control | Treated animals | Control | Treated animals | Control |
| 2 | + | +++ | + | 0 | 0 | 0 |
| 4 | + | ++ | ++ | + | high: rounded vs low: mature vs | high: 0 low: vs directed toward the top of the wound |
| 6 | 0 | ++ | +++ | ++ | mature vs | High: elongated and mature vs |
| 15 | 0 | 0 | + | ++ | + | + |
| 30 | 0 | 0 | + | + | few vs | few vs |

It is evident from table II that the extracellular matrix matures to a greater extent, and at an early stage, in the animals treated with the dextran derivative than in the control group. In particular, the inflammatory cells are less numerous in the wounds treated with the dextran derivative as compared with the untreated wounds, which display a persistence of the inflammatory phenomenon. In the wounds treated with the dextran derivative, it is also noted that, apart from appearing at an early stage, the fibroblasts are orientated and produce a more substantial extracellular matrix.

Table III summarizes the state of the epidermis, when it is present, in terms of the number of days of healing, with the term "migration" indicating initiation of the reconstruction of the epidermis by means of keratinocyte migration.

Table III: Epidermis

TABLE III

| | Epidermis. | |
|---|---|---|
| Days of healing | Treated animals | Control |
| 2 | Absence | absence |
| 4 | Migration | migration |
| 6 | Reconstituted and differentiated | migration |

TABLE III-continued

| | Epidermis. | |
|---|---|---|
| Days of healing | Treated animals | Control |
| 15 | Mature | reconstituted and in maturation |
| 30 | mature | mature |

Classically, regeneration of the epidermis involves migration of the cells of the dermis, followed by a reconstruction phase during which the cells proliferate, then maturation of the regenerated epidermis. It is evident from table III that the epidermis is reconstructed markedly more rapidly in the animals treated with the dextran derivative than in the animals of the control group.

Table IV below summarizes the kinetics of the appearance of the growth factor TGF (Transforming Growth Factor) within the wounds in terms of the number of days of healing (0: absence of TGF ; +, ++ and +++: presence of TGF , in a quantity which is higher the greater the number of the + signs).

Table IV: Kinetics of the Appearance of the Growth Factor TGF

TABLE IV

| Kinetics of the appearance of the growth factor TGF. | | |
|---|---|---|
| Days of healing | Treated animals | Control |
| 2 | 0 | 0 |
| 4 | +++ | + |
| 6 | + | ++ |
| 15 | 0 | 0 |
| 30 | 0 | 0 |

It is evident from table IV that the kinetics of the appearance of the growth factor TGF differs in the animals treated with a dextran derivative as compared with the untreated animals: TGF appears in large quantity from D4 onward in the treated animals whereas it only appears substantially on D6 in the untreated animals and then only in lower quantity.

EXAMPLE 3

Different protocol for assessing the in-vivo action of a dextran derivative of the general formula $DMC_aB_bSU_c$ on skin healing.

a) Protocol

The animals employed are 13-week-old "hairless" rats on which dorsal skin incisions of 6 cm in length are made. Four subcutaneous stitches using resorbable twisted thread (polyglatine 910, Vicryl®, size 5/0, ETHICON, France), which are spaced at distances of 1.5 cm from each other, are inserted in order to enable the edges of the incision to be brought together and opposed.

The animals are divided up into two groups:

a first group of 10 rats is treated with a 50 μg/ml solution, in a PBS buffer, of a dextran derivative of the general formula $DMC_aB_bSu_c$ in which a=0.65, b=0.12 and c=0.33, a second group of 10 rats, which serves as the negative control and which is only treated with a physiological solution.

The wounds are treated once daily for 4 days with the abovementioned solutions by means of topical application using a compress which is soaked in said solutions. Two hours after having been treated, the wounds are covered with a sterile dressing. A study of the resistance of the scars to traction is carried out after 3 and 7 days (D3 and D7) using small skin strips which are removed from the wound. A tensiometer is employed to measure the maximum traction (in grams) exerted on these skin samples prior to rupture.

b) Results

The resistance of the wounds to rupture on D3 and D7 is as follows:

wounds treated with the dextran derivative: 1 500 grams (D3) and 2 200 grams (D7), wounds treated solely with a physiological solution: 900 grams (D3) and 1 200 grams (D7).

Figure 3:
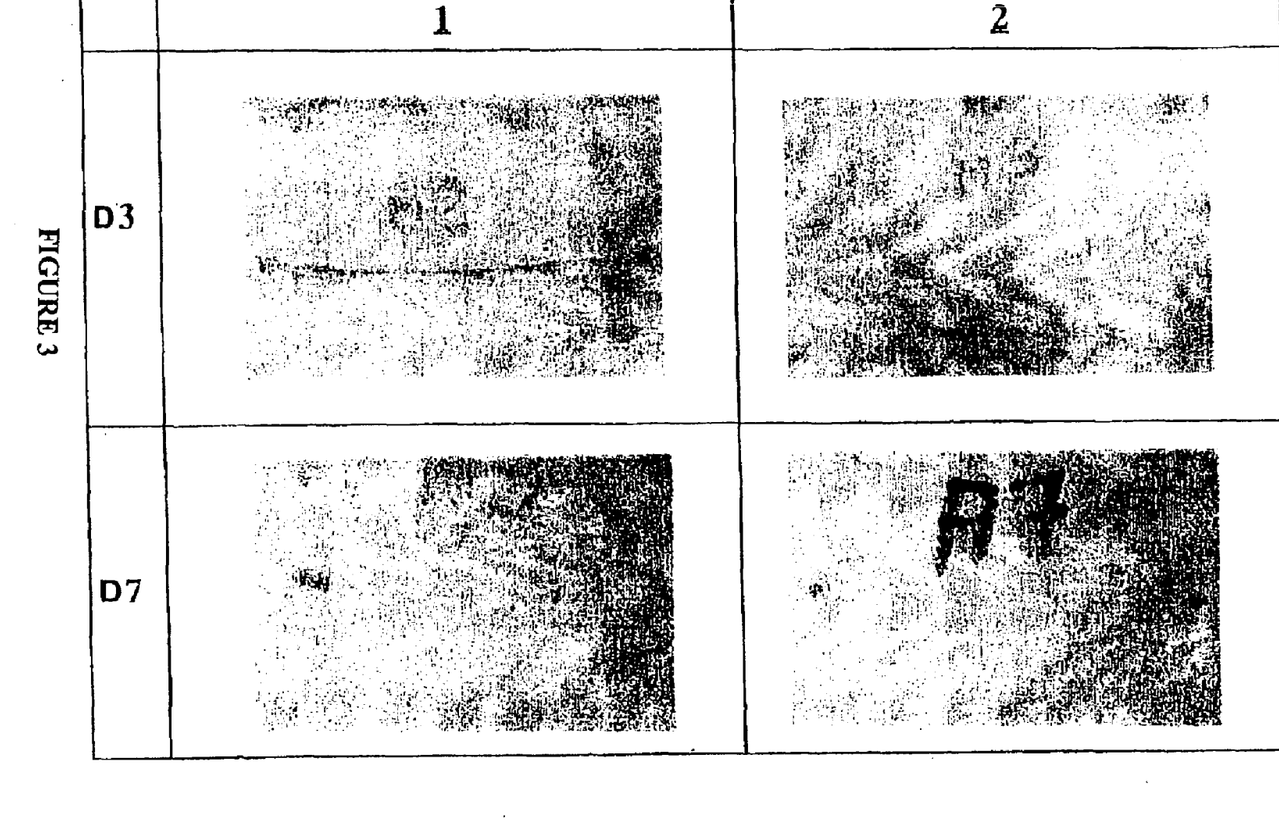
FIG. 3 shows the healing, after 3 and 7 days (D3 and D7), of dorsal skin incisions which were performed on rats, the wounds being treated either with a physiological solution (photographs in column 1) or with a solution of a dextran derivative of general formula $DMC_aB_bSu_c$ (photographs in column 2).

FIG. 3 shows photographs of the wounds which were only treated with a physiological solution (photographs in column 1) and of the wounds which were treated with the solution of the dextran derivative (photographs in column 2). A healing of much better quality is noted when the wounds are treated with the dextran derivative as compared with the wounds in the control animals.

EXAMPLE 4

In-vivo action of a dextran derivative of the general formula $DMC_aB_bSu_c$ on gastric healing.

a) Protocol

The animals employed are 12-week-old male Sprague-Dawley rats weighing from 200 to 250 g. Three batches of animals are used, with each consisting of 4 animals:

the first batch is treated with a dextran derivative of the general formula $DMC_aB_bSu_c$ in which a=0.75, b=0.25 and c=0.15, at the rate of 50 µg/kg, the second batch serves as the control, with the animals being treated with a native dextran T40 (Pharmacia Fine Chemical; weight average molecular mass $M_w$: 37 500 g/mol; $M_w/M_n$: 1.7, with $M_n$ representing the number average mass), at the rate of 50 µg/kg, the third batch is treated with prostaglandin E2 (Sigma; dose of 10 µg/kg), which has the effect of protecting the gastric mucosa against irritant products which induce a local inflammatory reaction. This batch therefore corresponds to a positive control.

The dextran derivative, the native dextran and the prostaglandin E2 are dissolved in physiological saline and administered orally to the animals.

The animals are sacrificed at different stages of healing, namely on D2, D4, D7 and D14, with the healing process being considered on days from the date on which the gastric irritation is induced. The gastric mucosa is recovered with a view to carrying out two studies:

quantification of the impairment of the gastric mucosa, isolation of the receptors for the following growth factors (EGF: Epidermal Growth Factor; PDGF Platelet-Derived Growth Factor and TGF: Transforming Growth Factor). This is because these growth factors are known to play an important role in gastric healing: TGF and EGF control cell proliferation by binding to their receptors whereas EGF promotes tissue restoration and the appearance of microvessels.

b) Results

Impairment of the Gastric Mucosa

Table V represents a compilation of the results of the macroscopic study of the inflammatory reaction in the gastric mucosa, with the study being effected in accordance with the following scale:

(0) Normal mucosa.

(+) Small superficial hemorrhagic striae.

(++) Short and broad superficial hemorrhagic striae.

(+++) Long and broad superficial hemorrhagic striae.

(++++) Perforations.

Table V: Impairment of the Gastric Mucosa

TABLE V

| | Impairment of the gastric mucosa. | | |
|---|---|---|---|
| Days | Dextran derivative | Prostaglandin E2 | Dextran T40 |
| D2 | ++ | ++ | +++ |
| D4 | + | + | +++ |
| D7 | + | + | ++ |
| D14 | 0 | 0 | ++ |

It can be seen from table V that the dextran derivative exerts effects which are comparable to those exerted by prostaglandin E2 but which are much superior to those exerted by dextran T40.

These results express the fact that the dextran derivative is able to protect the endogenous growth factors which are responsible for accelerating the healing of the gastric mucosa.

Growth Factor Receptors

Gastric healing is evidenced by an increase in receptors for two growth factors: EGF and PDGF. On day D4, the group treated with the dextran derivative exhibits from 1.7 to 1.8 times more receptors for these two growth factors than does the group treated with dextran T40. On day D7, the quantity of receptors for these two growth factors is 3 times greater in the group treated with the dextran derivative than in the group treated with dextran T40.

EXAMPLE 5

In-vivo action of a dextran derivative of the general formula $DMC_aB_bSu_c$ on muscle healing.

a) Protocol

The animals employed are 12-week-old male Wistar rats weighing from 200 to 300 g. Two batches of animals are used, with each consisting of 6 rats.

The protocol adopted is as follows: after anesthesia with ether, the muscles of the hind legs are released from the anterior compartment of the leg and injured mechanically by applying, for 10 seconds, a constant pressure along the whole of the length of the muscle using a Péan forceps maintained at the second notch.

The muscle is then replaced in its compartment after having been given an injection of 200 µl of either a 20 µg/ml solution of a dextran derivative of the general formula $DMC_aB_bSu_c$ in which a=0.75, b=0.25 and c=0.15 (right leg) or a physiological solution (left leg). The muscle is left in place for 3 minutes in order to allow the product to diffuse and the skin is then sutured.

The treated muscles (right and left hind legs) are removed after 7 days and frozen at −150° C. 10 µm transverse sections are then made in the median region of the muscle. The dried sections are stained with Gomori's trichrome stain.

b) Results

Table VI represents a compilation of a morphometric analysis of a number of fibers and their diameter, with the analysis being carried out on micrographic montages corresponding to a transverse hemisection of the muscle.

Table VI: Morphometric Analysis of the Muscles

TABLE VI

Morphometric analysis of the muscles

|  | Muscle treated with the dextran derivative | Muscle treated with the physiological saline |
|---|---|---|
| Diameter of the muscles (mm) | 6.5 ± 0.3 | 4.3 ± 0.2 |
| Number of muscle fiber bundles per section | 21 ± 2 | 11 ± 3 |
| Number of fibers per fiber bundle | 78 ± 10 | 65 ± 5 |
| Density of the fibers (number/mm$^2$) | 722 ± 52 | 83 ± 12 |

It can be seen from table VI that the muscles treated with the dextran derivative regenerate more rapidly than do the untreated muscles: the density of fibers is clearly higher than that in the muscles which were only given a physiological saline solution. The number of muscle fiber bundles, and the diameter of the muscles, provide evidence, respectively, of a muscle reorganization which is accelerated, and of a degree of muscle maturation which is improved, when the muscle is treated with the dextran derivative.

EXAMPLE 6

In-vivo action of a dextran derivative of the general formula $DMC_aB_bSu_c$ on ocular healing.

a) Protocol

20 New Zealand white rabbits (10 males and 10 females) are used, with the rabbits being 1 year old and weighing from 2.5 to 3 kg; a 5.5 mm filter soaked in a 1N solution of sodium hydroxide was placed for 60 seconds on the right eye of these rabbits, which were then divided up into 4 groups of 5 animals each:

the first group is treated three times daily with 100 µl of a solution containing 0.1 ng of FGF-2 (Fibroblast Growth Factor-2);

the second group is treated three times daily with 100 µl of an isotonic solution containing 50 µg of a dextran derivative/ml of the general formula $DMC_aB_bSu_c$ in which a=0.75, b=0.31 and c=0.34;

the third group is treated three times daily with 100 µl of a solution containing 0.1 ng of FGF-2 and 50 µg of the above-mentioned dextran derivative/ml;

the fourth group (control group) is treated three times daily with 100 µl of a PBS buffer solution.

The speed of ocular healing in the four groups of animals is compared by means of histological studies carried out on days D1, D2, D4, D6 and D8.

b) Results

The histological studies which were carried out show that the duration of ocular healing, expressed in accordance with a mean for each group of animals, is 4 days in the case of the third group, 5 days in the case of the first group, 6 days in the case of the second group and 8 days in the case of the control group. The ocular healing is therefore more rapid in the animals treated with the dextran derivative than in the control group. It is also noted that the healing takes place at an earlier stage when the dextran derivative is combined with a growth factor, as compared with when the dextran derivative is used or when the growth factor is used on its own, thereby demonstrating the protective and potentiating effect of the dextran derivative used in the compositions of the present invention vis-à-vis growth factors.

EXAMPLE 7

In-vivo anticomplementary action of a dextran derivative of the general formula $DMC_aB_bSu_c$.

a) Protocol

The animals employed are 12-week-old Sprague-Dawley male rats weighing from 200 to 300 g. Three batches of animals are used, with each batch consisting of 5 rats:

the first batch is given an injection of 500 µl of a solution containing Sephadex® G25 at the rate of 20 µg (Sephadex® is an activator of the alternative pathway of the complement system in humans), the second batch is given an injection of 500 µl of a solution containing Sephadex® G25 at the rate of 20 µg and 50 µg of native dextran (40 000 g/mol), the third group is given an injection of 50 µl of a solution containing Sephadex® G25 at the rate of 20 µg and 50 µg of a dextran derivative of the general formula $DMC_aB_bSu_c$ in which a=0.60, b=0.35 and c=0.25.

Lambda-carrageenan can also be used as an activator of the complement system in place of the Sephad® in accordance with the following protocol, which leads to the same results as those given below:

the first batch of animals is given an injection of 200 µl of a 1% (m/V) solution of lambda-carrageenan in 0.9% of NaCl, the second batch of animals is given an injection of 200 µl of this solution of lambda-carrageenan followed (30 minutes later) by an injection of 100 µl of the dextran derivative, the third batch of animals is given an injection of 200 µl of this solution of lambda-carrageenan followed (30 minutes later) by an injection of 100 µl of a 0.9% saline solution.

Cleavage of the C3 protein is determined by means of immunoelectrophoresis using an anti-C3 antibody.

The anticomplementary action is studied by means of a hemolytic or CH50 assay, in accordance with a protocol in which the serum of the rats, withdrawn at different time intervals, is activated by sheep erythrocytes which are sensitized by rabbit antibodies directed against sheep red blood cells (EA). By definition, one CH50 unit corresponds to the concentration of complement proteins (contained in one milliliter of serum) which is capable of inducing the hemolysis of 50% of $2\times10^7$ activated EAs in a reaction medium where the volume, the temperature and the reaction time are kept constant. The number of hemolytic sites per cell is calculated.

b) Results

An immunoelectrophoresis using an anti-C3 antibody, carried out on the serum of the rats which were given the dextran derivative (the third batch of animals), does not show any cleavage of the C3 protein, contrary to the sera of the rats which were given the native dextran and/or the Sephadex® (first and second batches of animals).

The native dextran did not have any effect on inhibition of the activation of the complement.

Figure 1:
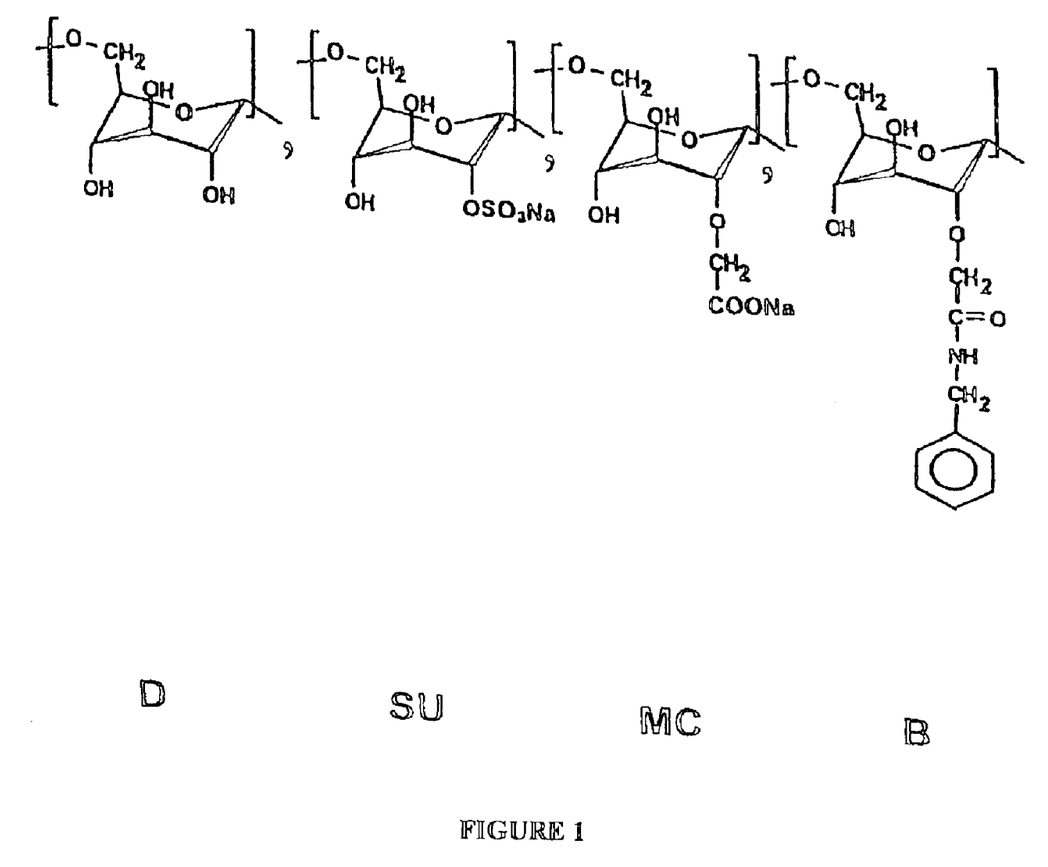
FIG. 1 diagrammatically illustrates the structure of a dextran which is substituted by the different chemical groups which are attached to the glucoside units; the position of the substituent on the different carbons of the glucoside-based units is shown in position 2, by way of example.
Figure 2:
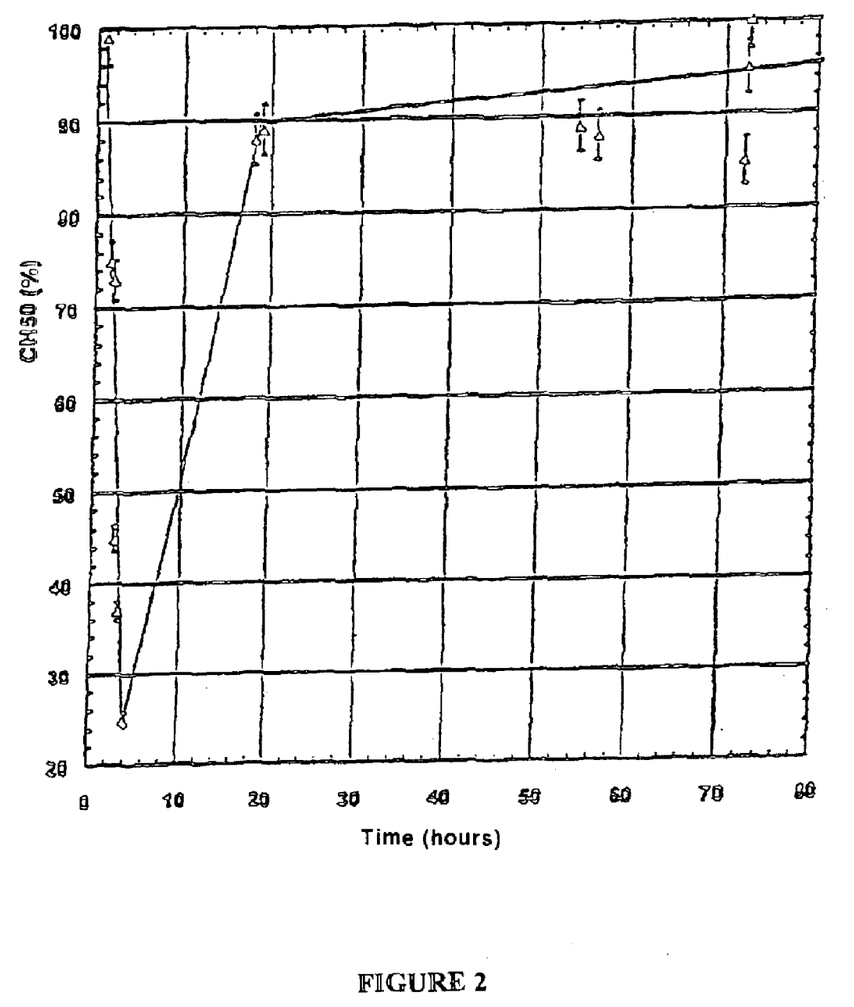
FIG. 2 illustrates the anticomplementary activity of a dextran derivative of general formula $DMC_aB_bSu_c$; in this figure, the CH50 (%), which is measured as indicated in example 5, is depicted in terms of the time (hours)

The dextran derivative which is used in the pharmaceutical composition according to the invention induces very rapid inhibitory action of the complement, as shown in FIG. 2, which depicts the CH50 (%) plotted against time (hours).

This continues for 4 hours after the injection. The CH50 returns to its initial level 20 hours after the injection.

Although embodiments, compositions, examples, uses and processes of the invention for formulating pharmaceutical compositions will wound healing or anti-complementary activity comprising a dextran derivative have been shown and described, it is to be understood that various modifications, variations and rearrangements of constituents, components or parts of the composition and its preparation, as well as other examples and uses of the invention, can be made by those skilled in the art without departing from the novel spirit and scope of the invention.

What is claimed is:

1. A pharmaceutical composition which has a healing action and which comprises:
   (1) at least one dextran derivative of the general formula $DMC_aB_bSu_c$ in which:
   D represents a dextran chain,
   MC represents methylcarboxylate groups,
   B represents carboxymethylbenzylamide groups,
   Su represents sulfate groups,
   a, b and c represent the degree of substitution (ds), expressed with respect to the number of free hydroxyl functions in a glucoside unit of the dextran, with MC, B and Su groups, respectively; with a being $\geq 0.6$, b being $\geq 0.1$ and c being between 0.1 and 0.5,
   which products exhibit a homogeneity in the distribution of the chain sizes which is illustrated by an elution profile of the symmetrical Gaussian type in high-performance steric exclusion chromatography and a homogeneity in the distribution of the charged chemical groups which is illustrated by an elution profile having a single symmetrical peak in low-pressure ion exchange chromatography,
   (2) and also at least one pharmaceutically acceptable excipient, with said dextran derivative being present at a unit dose of between 0.1 and 50 mg.

2. The pharmaceutical composition as claimed in claim 1 wherein said composition has an action on the healing of the gastric mucosa and is adapted for oral-administration.

3. The pharmaceutical composition as claimed in claim 2, wherein the unit dose of said dextran derivative is between 1.5 and 10 mg.

4. The pharmaceutical composition as claimed in claim 2, wherein said composition is present in the form of a gel, a gastric dressing, a syrup or a potable solution.

5. The pharmaceutical composition as claimed in claim 2, wherein said dextran derivative is enclosed in a gastric juice resistant enclosure.

6. The pharmaceutical composition as claimed in claim 1, wherein the unit dose of said dextran derivative is between 0.5 and 50 mg.

7. A pharmaceutical composition as claimed in claim 1, wherein said composition has an action on ocular healing and is present in the form of eye drops or an ophthalmic ointment.

8. The pharmaceutical composition as claimed in claim 7, wherein the unit dose of said dextran derivative is between 0.1 and 10 mg.

9. A pharmaceutical composition which has an action on skin healing, which is adapted to topical administration and which comprises:
   (1) at least one dextran derivative of the general formula $DMC_aB_bSu_c$ in which:
   D represents a dextran chain,
   MC represents methylcarboxylate groups,
   B represents carboxymethylbenzylamide groups,
   Su represents sulfate groups,
   a, b and c represent the degree of substitution (ds), expressed with respect to the number of free hydroxyl functions in a glucoside unit of the dextran, with MC, B and Su groups, respectively; with a being $\geq 0.6$, b being $\geq 0.1$ and c being between 0.1 and 0.5,
   which products exhibit a homogeneity in the distribution of the chain sizes which is illustrated by an elution profile of the symmetrical Gaussian type in high-performance steric exclusion chromatography and a homogeneity in the distribution of the charged chemical groups which is illustrated by an elution profile having a single symmetrical peak in low-pressure ion exchange chromatography,
   (2) and also at least one pharmaceutically acceptable excipient,
   with said dextran derivative being present at a concentration of less than 10% by weight/volume.

10. A pharmaceutical composition which is present in the form of an isotonic solution, has an anticomplementary action and which comprises:
    (1) at least one dextran derivative of the general formula $DMC_aB_bSu_c$ in which:
    D represents a dextran chain,
    MC represents methylcarboxylate groups,
    B represents carboxymethylbenzylamide groups,
    Su represents sulfate groups,
    a, b and c represent the degree of substitution (ds), expressed with respect to the number of free hydroxyl functions in a glucoside unit of the dextran, with MC, B and Su groups, respectively; with a being $\geq 0.3$, b being $\geq 0.1$ and c being between 0.1 and 0.4,
    which products exhibit a homogeneity in the distribution of the chain sizes which is illustrated by an elution profile of the symmetrical Gaussian type in high-performance steric exclusion chromatography and a homogeneity in the distribution of the charged chemical groups which is illustrated by an elution profile having a single symmetrical peak in low-pressure ion exchange chromatography,
    (2) and also at least one pharmaceutically acceptable excipient,
    with said dextran derivative being present at a unit dose of between 5 and 30 mg.

11. A dressing, characterized in that it is soaked with the pharmaceutical composition as claimed in claim 9.

* * * * *